United States Patent [19]
Alers et al.

[11] 4,289,030
[45] Sep. 15, 1981

[54] NONDESTRUCTIVE TESTING UTILIZING HORIZONTALLY POLARIZED SHEAR WAVES

[75] Inventors: George A. Alers, Albuquerque, N. Mex.; Robert B. Thompson; Carmine F. Vasile, both of Thousand Oaks, Calif.

[73] Assignee: Rockwell International Corporation, El Segundo, Calif.

[21] Appl. No.: 63,027

[22] Filed: Aug. 1, 1979

[51] Int. Cl.³ .............................................. G01N 29/04
[52] U.S. Cl. ........................................ 73/588; 73/637; 73/643
[58] Field of Search ................. 73/643, 588, 622, 637, 73/638, 640

[56] References Cited
U.S. PATENT DOCUMENTS

| | | | |
|---|---|---|---|
| 3,233,449 | 2/1966 | Harmon | 73/622 |
| 3,302,453 | 2/1967 | Wood et al. | 73/622 |
| 3,850,028 | 11/1974 | Thompson et al. | 73/643 |
| 4,092,868 | 6/1978 | Thompson et al. | 73/643 |
| 4,127,035 | 11/1978 | Vasile | 73/643 |
| 4,217,782 | 8/1980 | Pont | 73/637 |

*Primary Examiner*—Anthony V. Ciarlante
*Attorney, Agent, or Firm*—H. Fredrick Hamann; Craig O. Malin; John J. Deinken

[57] ABSTRACT

Disclosed is a nondestructive test device for detecting a flaw proximate to a welded seam in a pipe, including an electromagnetic acoustic transmitting transducer for generating a horizontally polarized shear wave in the wall of the pipe, a high frequency generator operatively connected to the transmitting transducer for energizing the transducer, an electromagnetic acoustic receiving transducer for responding to a horizontally polarized shear wave within the wall, an amplifier operatively connected to the receiving transducer for boosting the response signal of the transducer, and an indicating instrument for receiving and displaying the amplified response signal. In the test method disclosed, a horizontally polarized shear wave is generated in the wall, the pipe is monitored to detect a reflected horizontally polarized shear wave, and a time-dependent representation of the amplitude of the reflected wave is displayed. The wave generating, monitoring, and displaying steps are repeated along a length of the pipe to provide a comprehesive flaw inspection of that length of the pipe. The times of arrival of the generated and reflected waves are correlated to determine the circumferential position of the flaw.

7 Claims, 5 Drawing Figures

NONDESTRUCTIVE TESTING UTILIZING HORIZONTALLY POLARIZED SHEAR WAVES

BACKGROUND OF THE INVENTION

This invention relates to apparatus and methods for nondestructive testing, and is concerned in particular with the use of ultrasonic techniques in nondestructive testing.

Nondestructive methods are preferable for test situations where the comprehensive evaluation of inservice machinery, assembled components, or new products is required. Nondestructive techniques are particularly desirable, for example, in testing the materials employed in structures such as tracked vehicle rails, vessels and conduits for pressurized gas or steam, and pipelines. In such applications, it is imperative that the test method utilized reveal any significant flaws or imperfections so that potentially costly equipment failures and other undesirable consequences may be prevented.

Among the various techniques of nondestructive testing which are available, noncontact test techniques, which do not require physical contact between the testing apparatus and the item tested, are especially advantageous, since such techniques may be implemented with the additional advantages of high speed operation, good performance in extreme temperature environments, the ability to operate in inaccessible locations by remote control, and a need for only minimal subsequent cleanup operations.

One particular testing application, for example, in which nondestructive, noncontact testing techniques are useful is the inspection of a pipeline built from sections of pipe which are welded together and which are manufactured with longitudinal welded seams. A somewhat detailed discussion of the pipeline testing situation will serve to illustrate the state of the art, and its limitations, for nondestructive testing in general.

An inspection of the structural integrity of such a pipeline has commonly been performed at the pipe manufacturing location for the longitudinal weld and at the pipeline installation site for the girth welds joining the sections of pipe. A detailed x-ray examination of the girth welds is often performed before a pipeline is buried, but inspection of the longitudinal welds is typically deferred until a hydraulic pressure test is performed on a sample section of the installed pipeline. A failure in the pressure test can frequently be traced to cracks or other defects in or near the weld which escaped detection in earlier inspections or which were formed in the pipe during delivery, storage, or handling of the pipe prior to installation in the pipeline.

Since the hydraulic test is relatively expensive and further is not performed until after the completion of the pipeline construction phase, the cost of an earlier nondestructive inspection could be justified where such a test would ensure the detection of any defects in or near the longitudinal pipe weld which were large enough to cause a failure of the hydraulic pressure test.

Noncontact ultrasonic testing procedures and apparatus are known which potentially could be used in such a testing environment. Electromagnetic acoustic transducers (EMATs), for example, some of which are disclosed in U.S. Pat. Nos. 3,850,028 and 4,127,035, may be utilized to generate an ultrasonic wave in an electrically conductive or magnetic material through the interaction of a static magnetic field and a dynamic electromagnetic field. Cracks or other defects which are present in the material will affect the transmission or reflection characteristics of the waves in the material. Those changes may be measured, by an EMAT or other suitable transducer, and utilized in characterizing the part as acceptable or unacceptable for its intended use. Ultrasonic testing procedures have been adapted for use in pipeline inspections, as disclosed, for example, in U.S. Pat. No. 4,092,868.

Difficulties have been encountered, however, when such ultrasonic test methods are employed in an attempt to evaluate an object which contains a known discontinuity or inhomogenity. Such a discontinuity might be due to a weld, as in the type of pipeline discussed above, or might be caused by some other similar aspect of the structure of an object. It has been found that such a discontinuity tends to cause a disturbance in the reflection and refraction of ultrasonic waves which is so large that the effects due to the presence of cracks or defects near the discontinuity tend to be obscured, effectively rendering such defects undetectable by prior art ultrasonic methods.

Consequently, a need has developed in the art for an ultrasonic nondestructive testing technique which is capable of detecting flaws or imperfections in or near a known discontinuity or inhomogeneity in a material.

SUMMARY OF THE INVENTION

It is a general object of this invention to provide a new and improved method for performing a nondestructive evaluation of a test object.

A nondestructive test method for detecting an imperfection in an object includes, according to the invention, the steps of:

(a) generating a horizontally polarized shear wave in the object, and (b) monitoring the object to detect a reflected horizontally polarized shear wave, the method thereby being adapted to detect imperfections in the object which reflect a horizontally polarized shear wave, while exhibiting relative insensitivity to the presence in the object of a discontinuity, such as a weld, which does not effectively reflect a horizontally polarized shear wave.

In a more particular embodiment, the method is adapted to detect a flaw proximate to a welded seam in a pipe, and includes the steps of:

(a) generating a horizontally polarized shear wave in the wall of the pipe, (b) monitoring the pipe to detect a reflected horizontally polarized shear wave in the wall, (c) displaying a time-dependent representation of the amplitude of the reflected wave, the form of the time-dependent display being indicative of the presence or absence of a flaw in the pipe, (d) repeating, at sequential locations along a preselected length of the pipe, the steps of generating a horizontally polarized shear wave, monitoring to detect a reflected wave, and displaying a time-dependent representation, thereby accomplishing a comprehensive flaw inspection of the preselected length of pipe, and (e) correlating the times of arrival of the generated and reflected waves to determine the circumferential location of the flaw.

Examples of the more important features of the invention have been broadly outlined above in order to facilitate an understanding of the detailed description that follows and so that the contributions which this invention provides to the art may be better appreciated. There are, of course, additional features of the invention, which will be described below and which are included within the subject matter of the appended claims.

BRIEF DESCRIPTION OF THE DRAWINGS

Additional objects, features, and advantages of the present invention will become apparent by referring to the detailed description below of the preferred embodiments in connection with the accompanying drawings, wherein like reference numerals refer to like elements throughout all the figures. In the drawings.

DETAILED DESCRIPTION OF A PREFERRED EMBODIMENT

Figure 1:
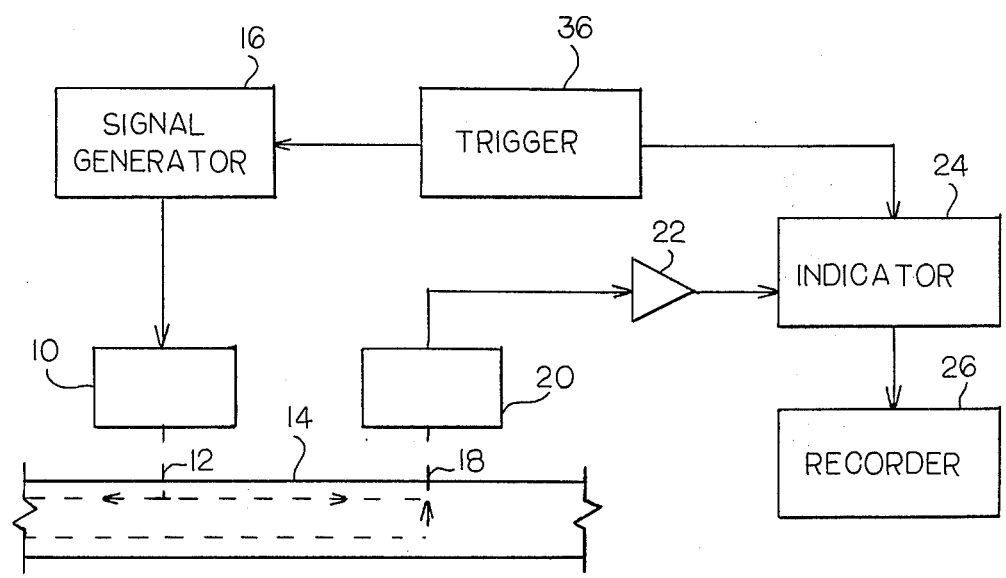
FIG. 1 is a schematic block diagram illustrating the configuration of a nondestructive test device constructed according to the present invention.

Now referring to the drawings, and first to FIG. 1, a schematic block diagram of a test device constructed according to the present invention is illustrated. A transmitting transducer 10 induces a horizontally polarized shear wave 12 in a pipe wall 14 when energized by a signal from a signal generator 16. A reflected horizontally polarized shear wave 18 is detected by a receiving transducer 20, the output of which is processed by an amplifier 22, an indicating instrument 24, and a recorder 26 to provide data useful in determining whether a flaw exists in the pipe.

Although the method of this invention will be described herein with respect to a preferred embodiment of the invention which is adapted for the testing of welded pipe, it should be understood that the invention is not limited to applications in the pipeline testing environment, but may be used to advantage in many other testing environments, as will be appreciated by those skilled in the art.

It is well known in the art that ultrasonic waves propagating in an elastic medium will be perturbed by the presence of flaws or other imperfections in the medium. This effect has been utilized to develop nondestructive test methods which employ ultrasonic waves to detect defects in materials.

A number of specific types of ultrasonic waves, such as L (longitudinal), SV (vertical shear), and SH (horizontal shear), may be generated and propagated in a solid material.

As a particular example of the generation of ultrasonic waves, such waves may be generated and detected in an electrically conductive or magnetic material through the use of electromagnetic acoustic transducers (EMATs). An EMAT operates in a manner analogous to an electric motor, i.e., when an electromagnetic field is applied to a conducting material in the presence of a D.C. or static magnetic field, eddy currents generated within the material will interact with the static field to exert forces on the material. By selecting an A.C. current of the appropriate frequency to create the electromagnetic field, the forces exerted may be used to generate ultrasonic waves at that frequency in the material. This phenomena may also be utilized in reverse for detection purposes, since an eddy current will be generated when the acoustic wave causes the conductive material to move in the presence of a D.C. magnetic field. This eddy current will induce a current in the coil of an EMAT. If the material being tested is also ferromagnetic, magnetostrictive forces will act in the material and will tend to further enhance the efficiency of an EMAT. Typical EMAT designs which may be used in ultrasonic testing applications are disclosed in U.S. Pat. Nos. 4,092,868 and 4,127,035, the teachings of which are incorporated herein by reference.

The prior art techniques utilizing ultrasonic waves for materials testing, however, have proven inadequate for the detection of flaws located near an inhomogeneity in the tested material. Steel pipe, for example, such as that commonly used in oil and gas pipelines, is manufactured from flat stock which is bent into a cylindrical shape and joined by a weld, the weld thus forming a longitudinal seam along the pipe. In conventional ultrasonic testing techniques, it has been found that such a pipe weld will strongly reflect the ultrasonic energy propagated in the pipe. Consequently, reflections from cracks or other imperfections located in the vicinity of the weld are likely to be obscured by the large response caused by the weld.

It is an outstanding feature of this invention to provide a method and apparatus for ultrasonic testing by which imperfections located near an inhomogeneity in a material may be detected. This invention is founded on the discovery that horizontally polarized shear (SH) ultrasonic waves experience minimal reflection when passing through a symmetric discontinuity, such as a weld, in a material, while SH waves are reflected relatively well from a flaw in the material. This effect appears to arise from the nonsymmetric geometry of a flaw which enters the material from one side. This characteristic may be used to advantage by designing an ultrasonic testing apparatus to selectively detect only horizontally polarized (SH) shear waves. The presence of reflected SH waves will then indicate that a symmetry breaking defect has been detected.

The usefulness of this discovery has been proven in tests on an experimental section of pipe which contained a number of identified flaws. A 36 inch diameter section of welded pipe 79 inches in length, with a wall thickness of 0.47 inches, was used for the test. In order to simulate various types of flaws in the pipe, the weld bead was ground off of both the inner and outer surfaces at from 0 to 50 cm from the left end of the pipe. A 23 cm square section of the pipe was cut out at 0–23 cm. A longitudinal saw cut 5.8 cm in length and through 47% of the wall thickness was made at 23 cm, while a similar cut 5.9 cm in length and through 24% of the wall was made at 39 cm. Further cuts were made in the weld at 74 cm (53% of wall and 6 cm long) and 90 cm (20% of wall and 4 cm long). A 12 cm, 25% crack at 132 cm, a 16.5 cm, 24% crack at 155 cm, and a 17 cm, 40% crack at 178 cm were introduced into the pipe wall approximately ⅛ inch from the weld bead.

Figure 2:
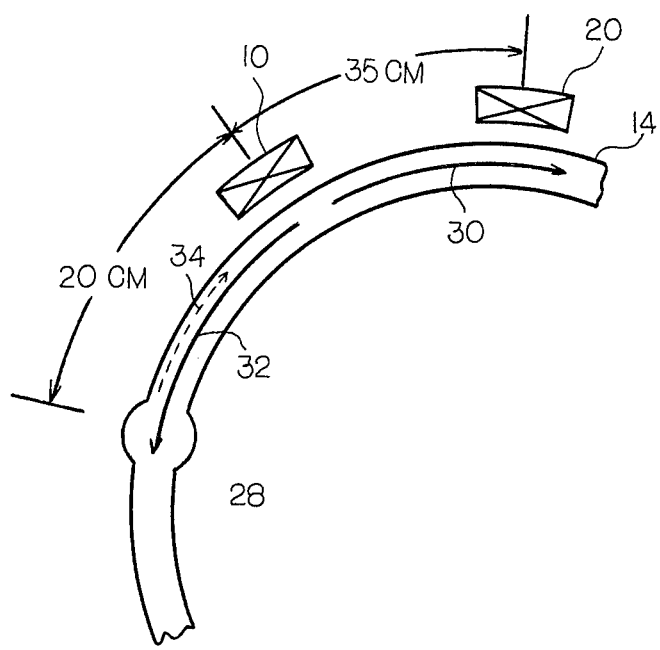
FIG. 2 is a cross-sectional representation of a pipe and associated transducers which illustrates the principal of operation of the present invention.

A transmitter and receiver pair of periodic magnet transducers, similar to those disclosed in U.S. Pat. No 4,127,035, was mounted on the test pipe in the configuration shown in FIG. 2, where the transmitting transducer 10 is mounted on the pipe wall 14 20 cm from the longitudinal weld bead 28, and receiving transducer 20 is mounted on the wall 35 cm from the transmitting transducer. Using an operating frequency of 130 KHz, the transmitting transducer 10 generated horizontal shear waves which propagated circumferentially in both directions, as indicated in FIG. 2 by the solid lines 30 and 32. A reflected horizontal shear wave is indicated by the dashed line 34.

Figure 3:
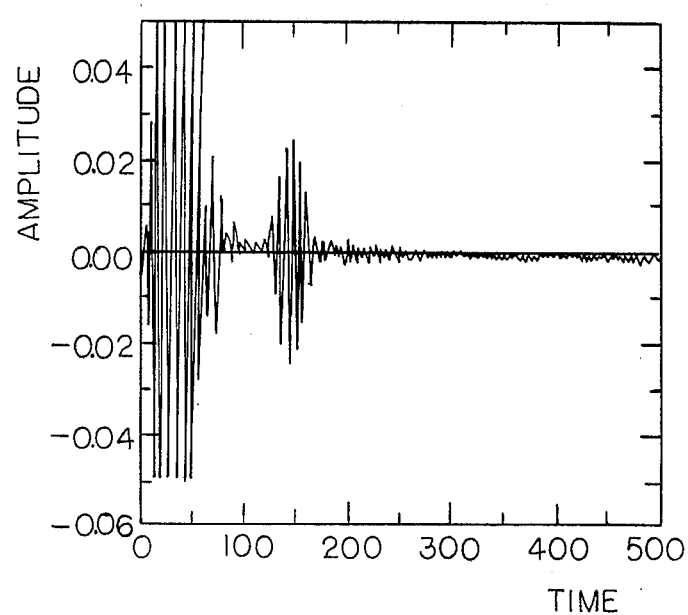
FIG. 3 depicts an oscilloscope trace for a particular test employing the present invention on a flaw free section of pipe.
Figure 4:
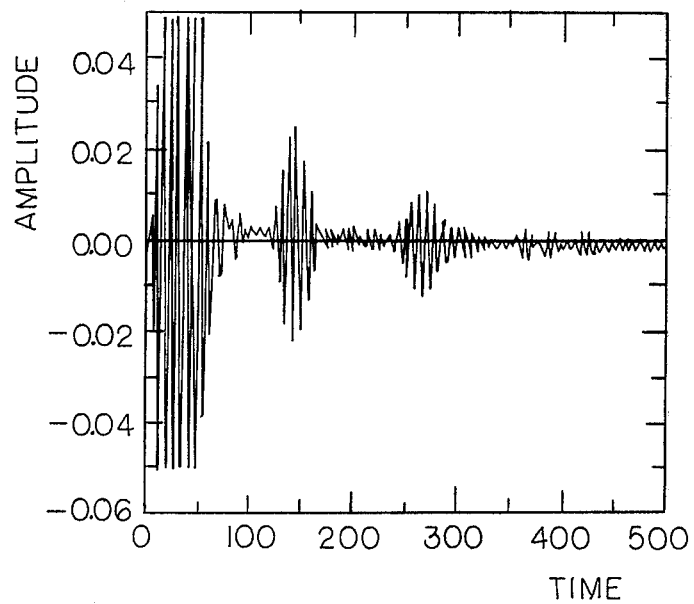
FIG. 4 depicts an oscilloscope trace for a particular test employing the present invention on a flawed section of pipe.

Now referring to FIG. 3, a computer printout representing the shear wave amplitude detected by the transducer 20 for a nonflawed section of pipe is illustrated. The signal arriving at 150 μsec corresponds to the SH wave which propagated directly from the transmitting transducer 10 to the receiving transducer 20 in a clockwise direction, as shown by line 30. Now referring to FIG. 4, a computer printout of the received SH wave amplitude is shown for a test run covering a flawed section of the pipe. As in FIG. 3, the signal at 150 μsec represents the directly propagated SH wave travelling in a clockwise direction. The signal at 260 μsec, however, corresponds to the SH wave which propagated from the transmitting transducer in a counterclockwise direction (line 32), was reflected by a defect in the weld 28, and thence travelled to the receiving transducer in a clockwise direction. The arrival times of the two signals in FIGS. 3 and 4 are consistent with the known propagation velocity of shear waves and the physical locations of the transducers relative to the weld in the test.

Thus, the test demonstrates the remarkable result that a good weld bead is a very poor reflector of horizontally polarized shear waves. Presumably, the fact that the weld represents a symmetrical mass loading on the pipe wall causes it to interact very poorly with shearing distortions which are polarized in the plane of the pipe wall and parallel to the weld bead, such as are associated with an SH wave. The fact that the crack which caused the reflection at 260 μsec in FIG. 4 was not symmetrically located relative to the center line of the pipe wall appears to cause it to be a strong reflector of horizontally polarized shear waves.

Figure 5:
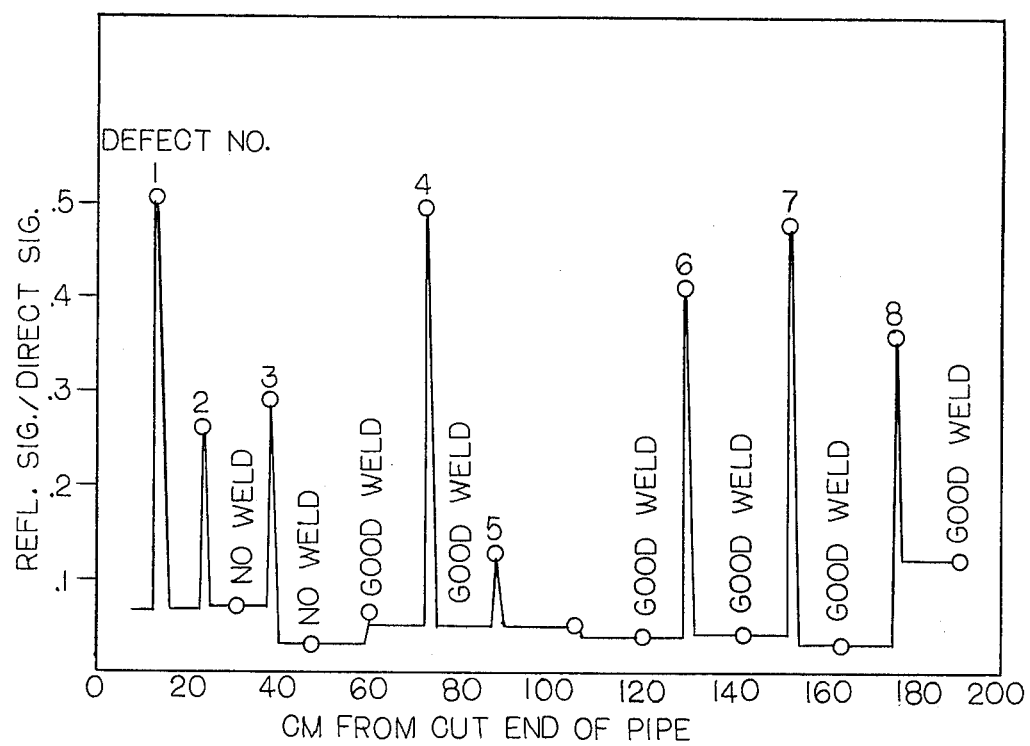
FIG. 5 is a graphical representation plotting relative signal amplitude versus test position for a sample of pipe.

To further verify the utility of this flaw detection technique, measurements were made of the amplitude of the SH wave signal reflected from the weld at each defect present in the test section of pipe and in the regions of good weld between the defects. Since the signal at 150 μsec can serve as a measure of the amplitude of the incident sound wave at any point, it was used to normalize the signal measurements. FIG. 5 provides a plot of the relative signal amplitude which was obtained as a function of position along the test pipe. As can be observed from the plot, the defective weld locations stand out in sharp contrast to areas with a good weld.

Now referring again to FIG. 1, an apparatus for practicing this invention is schematically illustrated. To begin a test sequence, the trigger circuit 36 is activated, causing the signal generator 16 to supply a high frequency pulse to the transmitting transducer 10. This pulse causes the transducer to generate a horizontally polarized shear (SH) wave, represented by the dashed line 12, in the pipe wall 14 travelling in both directions away from the transducer. The receiving transducer 20 detects the directly propagated portion of the generated SH wave and any reflected SH wave, as represented by dashed line 18. The resulting signal from the transducer 20 is amplified in the amplifier 22 and displayed by the indicating instrument 24. Instrument 24, which may typically be an oscilloscope, is triggered by the trigger circuit 36. A recorder 26 may also be provided, if necessary, to provide a record of the test results displayed by the instrument 24. The transducers 10 and 20 are preferably of the periodic permanent EMAT design, as disclosed in U.S. Pat. No. 4,127,035.

In conclusion, although typical embodiments of the present invention have been illustrated and discussed above, numerous modifications and alternative embodiments of the method of this invention will be apparent to those skilled in the art in view of this description. The invention may be of considerable utility, for example, in many applications which do not involve the testing of a pipeline. Accordingly, this description is to be considered as illustrative only and is provided for the purpose of teaching those skilled in the art the manner of performing the method of this invention. Furthermore, it should be understood that the forms of the invention depicted and described herein are to be considered as the presently preferred embodiment. Various changes may be made in the configurations, sizes, and arrangements of the components of the invention, as wil be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit attained through reading the above description of the invention.

What is claimed is:

1. A nondestructive test method for detecting an imperfection in an object near a symmetric discontinuity, comprising the steps of:
   generating a horizontally polarized shear wave in the object and directed toward the symmetric discontinuity; and
   monitoring the object to detect a horizontally polarized shear wave reflected from the imperfection,
   the method thereby being adapted to detect imperfections in the object which reflect a horizontally polarized shear wave, while exhibiting relative insensitivity to the presence in the object of discontinuities which do not reflect a horizontally polarized shear wave.

2. The method of claim 1, further comprising the step of correlating the time of generation of the wave and the time of detection of the reflected wave to locate the imperfection in the object.

3. The method of claim 1, wherein the object is a welded pipe and the method is used to detect flaws in the pipe.

4. The method of claim 3, wherein the method is performed within the interior of an installed pipeline.

5. A nondestructive test method for detecting a flaw proximate to a welded seam in a pipe, comprising the steps of:
   generating a horizontally polarized shear wave in the wall of the pipe and directed toward the welded seam;
   monitoring the pipe to detect a horizontally polarized shear wave reflected from the flaw in the wall; and
   displaying a time-dependent representation of the amplitude of the reflected wave, the form of the time-dependent display being indicative of the presence or absence of a flaw in the pipe.

6. The method of claim 5, further comprising the step of repeating, at sequential locations along a preselected length of the pipe, the steps of generating a horizontally polarized shear wave, monitoring to detect a reflected wave, and displaying a time-dependent representation, thereby accomplishing a comprehensive flaw inspection of the preselected length of the pipe.

7. The method of claim 6, further comprising the step of correlating the times of arrival of the generated and reflected waves to determine the circumferential location of the flaw.

* * * * *